(12) United States Patent
Ford

(10) Patent No.: US 8,337,538 B1
(45) Date of Patent: Dec. 25, 2012

(54) BED DEVICE FOR PROVIDING PHOTOTHERAPY TO INFANTS

(76) Inventor: Evatnor Ford, Calumet Park, IL (US)

( * ) Notice: Subject to any disclaimer, the term of this patent is extended or adjusted under 35 U.S.C. 154(b) by 386 days.

(21) Appl. No.: 12/792,454

(22) Filed: Jun. 2, 2010

(51) Int. Cl.
*A61N 5/06* (2006.01)
(52) U.S. Cl. ............... 607/88; 607/90; 607/91
(58) Field of Classification Search ........... 607/88, 607/90, 91
See application file for complete search history.

(56) References Cited

U.S. PATENT DOCUMENTS

| | | |
|---|---|---|
| 3,858,570 A | 1/1975 | Beld et al. |
| 4,809,677 A | 3/1989 | Mackin et al. |
| 5,006,105 A | 4/1991 | Sherard |
| 5,446,934 A | 9/1995 | Frazier |
| 5,792,214 A | 8/1998 | Larsson et al. |
| 6,905,457 B2 | 6/2005 | Mackin |
| 7,008,371 B2 | 3/2006 | Goldberg et al. |
| D567,948 S | 4/2008 | Tierney et al. |
| 7,442,163 B2 | 10/2008 | Ten Eyck et al. |
| 2007/0088410 A1 | 4/2007 | Chung et al. |

*Primary Examiner* — Armando Rodriguez

(57) ABSTRACT

An enclosed bed device for providing phototherapy to infants featuring a small bed base having a base enclosure, a base pad disposed in the base enclosure; a lid pivotally attached to the bed base, the lid has a lid enclosure; first fluorescent lights disposed in the lid enclosure and second fluorescent lights disposed in the base pad, the fluorescent lights are operatively connected to a power source; and a mesh cloth cover wrapped over the base pad, the mesh cloth cover is adapted to allow light from the second fluorescent lights in the base pad to pass from the base pad to the infant atop the base pad; wherein the base or lid either (i) is generally translucent, transparent, semi-translucent, semi-transparent, or tinted for viewing; or (ii) comprises a window for providing visual access.

10 Claims, 4 Drawing Sheets

BED DEVICE FOR PROVIDING PHOTOTHERAPY TO INFANTS

FIELD OF THE INVENTION

The present invention is directed to devices for providing phototherapy to infants suffering from hyperbilirubinemia, more particularly to an enclosed bed providing the infant adequate exposure to fluorescent lamps as well as providing visual access to the healthcare worker and parents.

BACKGROUND OF THE INVENTION

Hyberbilirubinemia is treated with the use of fluorescent lights. The newborn is placed on a fluorescent blanket or under fluorescent lamps in a crib or incubator The newborn may require more than one fluorescent lamp, in which case the plurality of fluorescent lamps can obstruct the view of the healthcare worker or parent. In addition, the infant often must be put on a cardiac monitor. In some cases, the infant can become cold because his/her skin is exposed.

The present invention features an enclosed bed device for providing phototherapy to infants. The bed device of the present invention can help eliminate the need to set up big sets of overpowering fluorescent lamps, which can obstruct the view of the newborn. Parents and healthcare workers can see the newborn while the newborn is receiving phototherapy. In some embodiments, the bed device helps eliminate the need to put a cardiac monitor on the newborn. Also, the bed device of the present invention can help the infant to stay warm.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features an enclosed bed device for providing phototherapy to infants. The enclosed bed device may comprise a small bed base having a bottom surface and side walls that together form a base enclosure, wherein a base pad is disposed in the base enclosure, the base pad is a comfortable pad on which an infant is placed; a lid pivotally attached to the bed base via a pivot means, the lid can pivot between multiple positions including an open position and a closed position respectively allowing and preventing access to the base enclosure of the bed base, the lid comprises a top surface and side walls that together form a lid enclosure; one or more first fluorescent lights disposed in the lid enclosure and one or more second fluorescent lights disposed in the base pad, the first fluorescent lights and second fluorescent lights are operatively connected to a power source; a mesh cloth cover wrapped over the base pad, the mesh cloth cover is adapted to allow light from the second fluorescent lights in the base pad to pass from the base pad to the infant atop the base pad; a floor base and a stem extending upwardly from the floor base, the bed base is disposed atop the stem, the stem is adjustable in length via a manual or electronic mechanism, wherein three or more wheels are disposed on the floor base for allowing transport of the enclosed bed device, one or more drawers or cabinets are disposed in either the stem or floor base; and a control panel operatively connected to the first fluorescent lights and second fluorescent lights for turning the lights on and off and for manipulating intensity of the lights; wherein the base or lid either (i) is generally translucent, transparent, semi-translucent, semi-transparent, or tinted for viewing; or (ii) comprises a window for providing visual access.

In some embodiments, the enclosed bed device further comprises one or more slots disposed in the base to allow cords to easily pass in and out of the base. In some embodiments, the lid is pivotally attached to a first side edge of the bed base. In some embodiments, the enclosed bed device further comprises a handle disposed on the lid. In some embodiments, the second fluorescent lights are fiber optic cords that run through the base pad. In some embodiments, the first fluorescent lights and second fluorescent lights are operatively connected to an electrical outlet via a plug. In some embodiments, the stem comprises an inner pole telescopically received in an outer pole. In some embodiments, the enclosed bed device further comprises a heating system for helping to warm the infant when in the bed device. In some embodiments, the enclosed bed device further comprises a temperature gauge or thermometer for measuring temperature in the base. In some embodiments, the enclosed bed device further comprises an IV pole holder disposed on the base.

DESCRIPTION OF PREFERRED EMBODIMENTS

Figure 1:
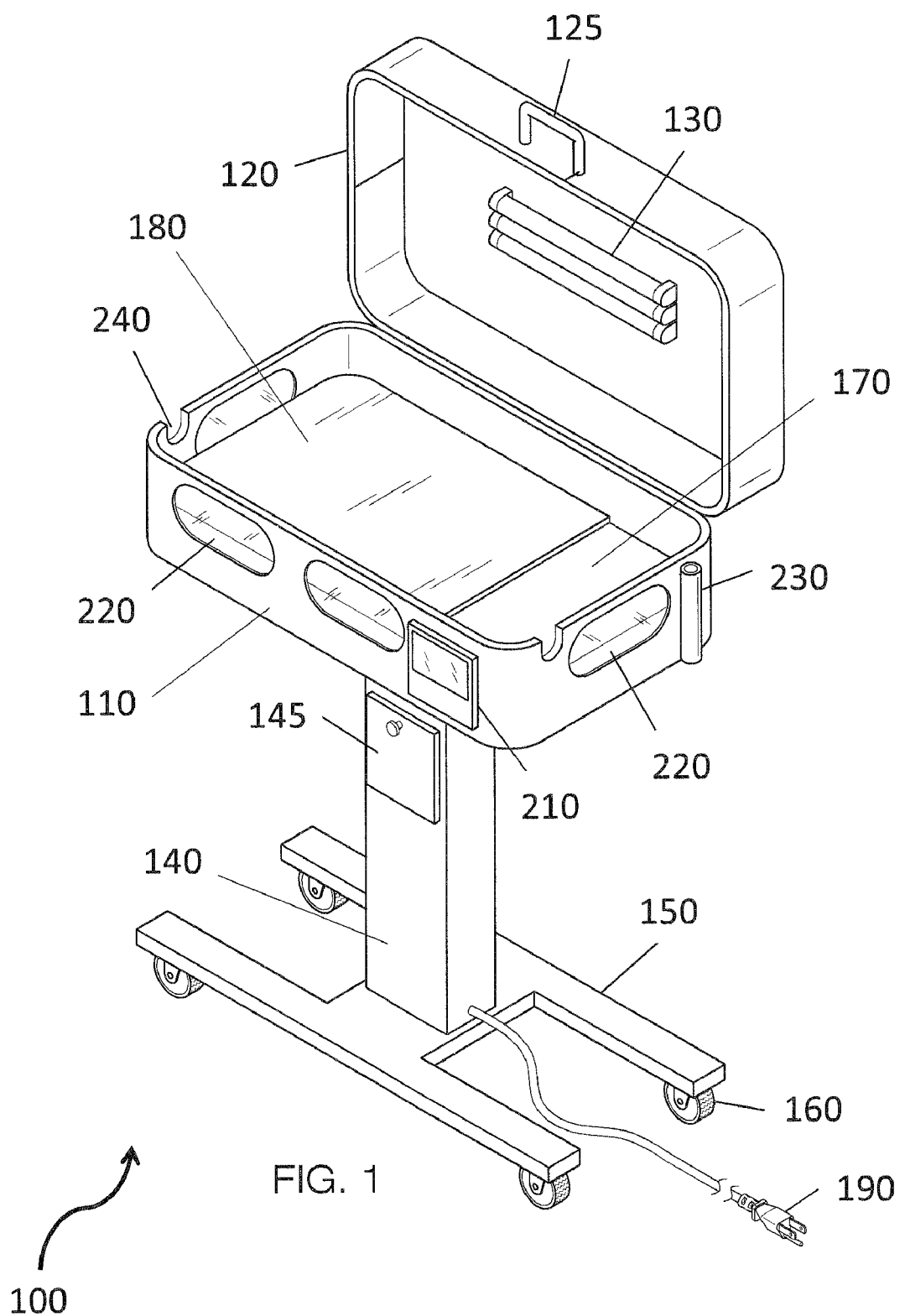
FIG. 1 is a first perspective view of the of the enclosed bed device of the present invention, wherein the lid is in the open position.
Figure 2:
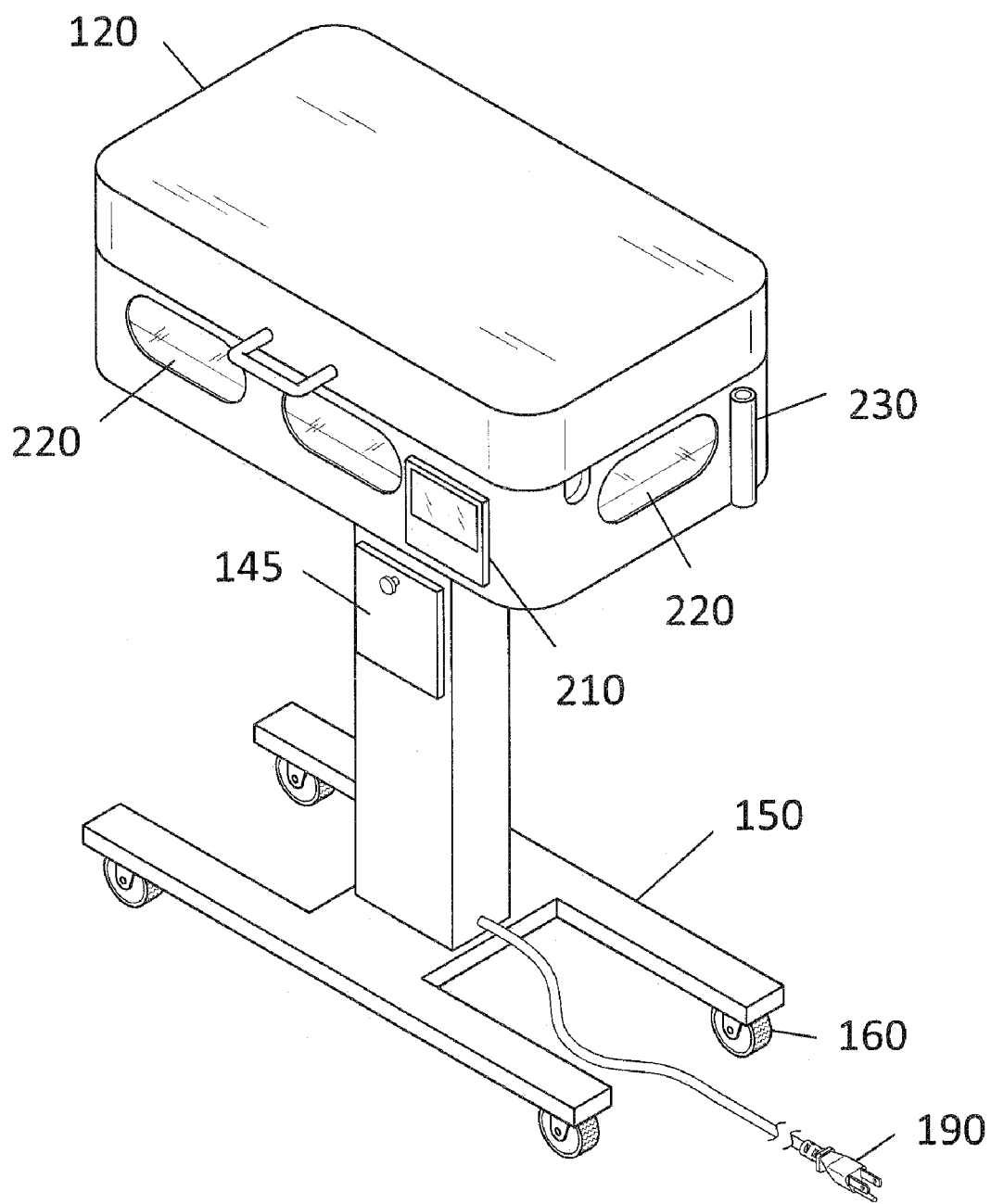
FIG. 2 is a second perspective view of the enclosed bed device of FIG. 1, wherein the lid is in the closed position.

Referring now to FIGS. 1-5, the present invention features an enclosed bed device 100 for providing phototherapy to infants. As shown in FIG. 1 and FIG. 2, the enclosed bed device 100 of the present invention comprises a small bed base 110 having a bottom surface, a first side wall, a second side wall, a third side wall, and a fourth side wall. Together, the side walls and bottom surface form a base enclosure. The newborn can be easily placed into and removed from the base enclosure.

A lid 120 is pivotally attached to the bed base 110, for example the first side edge of the bed base 110, via a pivot means (e.g., one or more hinges 128). The lid 120 can pivot between multiple positions including but not limited to an open position and a closed position respectively allowing and preventing access to the enclosure in the bed base 110. As shown in FIG. 1, the lid 120 comprises side walls and a top surface, wherein the side walls and top surface form a lid enclosure. In some embodiments, a handle 125 is disposed on the lid 120, for example on a side wall or top surface of the lid 120.

The base 110 and/or lid 120 may be clear (e.g., translucent, transparent, semi-translucent, semi-transparent, etc.) or can be slightly tinted for viewing.

One or more first fluorescent lights 130 are disposed in the lid enclosure on the top surface (see FIG. 1). The first fluorescent lights 130 resemble standard fluorescent lights used in phototherapy, which are well known to one of ordinary skill in the art. In some embodiments, the first fluorescent lights 130 can be turned on to various intensities, for example low intensity, medium intensity, and high intensity.

The bed base 110 is raised a certain distance above the ground surface (e.g., the floor) via a stem 140 and floor base 150. As shown in FIG. 1 and FIG. 2, the bed base 110 is disposed on the top end of the stem 140, and the floor base 150 is disposed on the bottom end of the stem 140. The floor base 150 comprises three or more wheels 160 (e.g., caster wheels), which allow the bed device 100 of the present invention to be transported as needed. In some embodiments, one or more drawers 145 or cabinets are disposed in the stem 140 or on the floor base 150. The drawers 145 may be used for a variety of purposes including but not limited to holding supplies such as diapers, etc.

Figure 3:
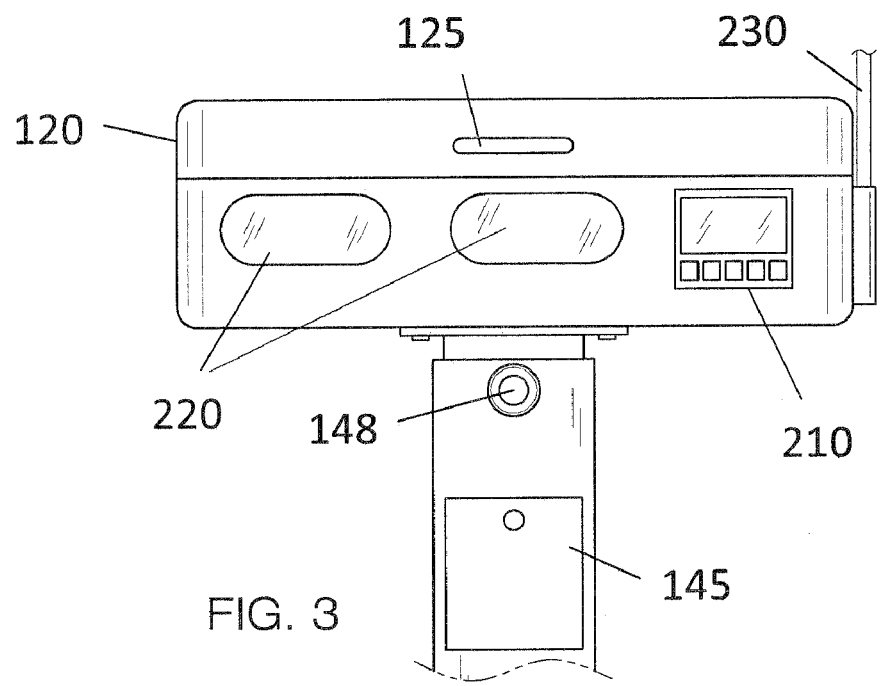
FIG. 3 is a front view of the enclosed bed device of FIG. 2.
Figure 4:
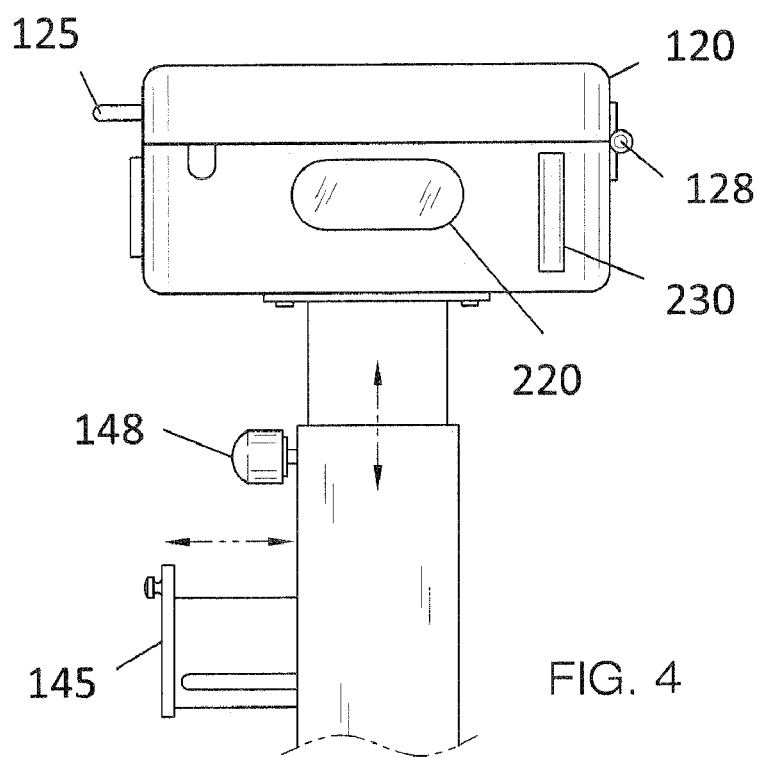
FIG. 4 is a side view of the enclosed bed device of FIG. 2.
Figure 5:
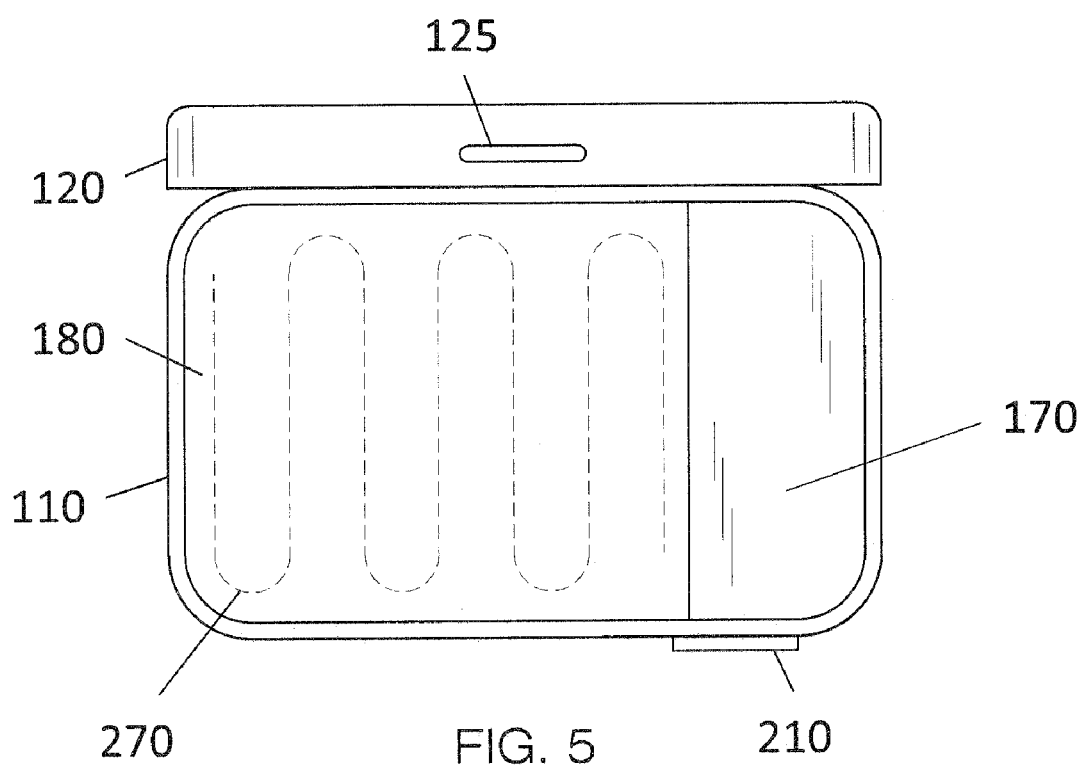
FIG. 5 is a top view of the enclosed bed device of FIG. 1.

As shown in FIG. 3 and FIG. 4, the stem 140 may comprise an inner pole telescopically received in an outer pole. The telescopic poles allow the stem 140 to expand and contract in length, allowing the base 110 to be positioned as needed. In some embodiments, the stem 140 can be expanded and contracted via a manual or an electronic system. Means for manually or electronically expanding and contracting shafts, poles, and tubes are well known to one of ordinary skill in the art. For example, in some embodiments, the shaft 140 comprises a spring-loaded button and aperture mechanism. In some embodiments, a locking knob 148 is used to secure the stem 140 at the desired height.

Disposed in the base enclosure on the bottom surface of the base 110 is a base pad 170 (e.g., flotation mattress). The base pad 170 (e.g., flotation mattress) is a comfortable pad on which the newborn is placed. One or more second fluorescent lights 270 are disposed in the base pad 170 (see FIG. 5). The second fluorescent lights 270 provide additional therapeutic light to the back of the infant. In some embodiments, the second fluorescent lights 270 are fiber optic cords that run through the pad 170 (e.g., a center region of the pad 170 where the infant is situated).

In some embodiments a cloth cover 180 is provided with the base pad 170, the cloth cover 180 being wrapped over the base pad 170 (or attached in other manners). In some embodiments, the base enclosure is small, preventing the infant from moving around too much (e.g., becoming entangled in the cloth cover 180). In some embodiments, the cloth cover 180 is a mesh cloth or variation thereof, for example a mesh pillow case-type cloth. The mesh helps to allow light from the second fluorescent lights 270 to pass from the base pad 170 to the infant (e.g., to expose the back of the infant). The cloth cover 180 is not limited to mesh. The infant is placed atop the cloth cover 180.

The first fluorescent lights 130 and/or second fluorescent lights 270 are operatively connected to a power source, for example a battery or an electrical outlet. In some embodiments, the first fluorescent lights 130 and/or second fluorescent lights 270 are operatively connected to an electrical outlet via a plug 190. Plugs for electrical outlets are well known to one of ordinary skill in the art.

The bed device 100 of the present invention further comprises a control panel 210 operatively connected to the first fluorescent lights 130 and/or second fluorescent lights 270 for manipulating the intensity and/or turning on and off the first fluorescent lights 130 and/or second fluorescent lights 270. The control panel 210 may be disposed on the base 110, for example a side wall. The control panel 210 is not limited to positioning on the base 110.

In some embodiments the base 110 and/or lid 120 is tinted. In some embodiments, one or more windows 220 are disposed in the base 110 and/or lid 120 for providing visual access to the base enclosure. In some embodiments, an IV pole holder 230 is disposed on the base 110, for example a side wall of the base 110.

As shown in FIG. 1, in some embodiments, one or more slots 240 are disposed in the base 110, for example the side walls of the base 110 at their respective top edges. The slots 240 allow cords to easily pass in and out of the base enclosure while allowing the lid 120 to sit flush atop the base 110.

In some embodiments, the bed device 100 further comprises a heating system for helping to warm the infant when in the bed device 100. In some embodiments, the bed device 100 of the present invention further comprises a temperature gauge or thermometer for measuring the temperature in the base and lid enclosures. The temperature gauge may be operatively connected to an alarm system (e.g., via a microprocessor), wherein the alarm system becomes activated if the temperature is too high. This can help the infant from becoming too hot.

The present invention also features a method of treating hyperbilirubinemia. The method comprises obtaining the bed device 100 of the present invention and placing the infant on the pad 170. The lid 120 can then be closed and the lights 130, 270 subsequently activated for a certain period of time (as needed).

Without wishing to limit the present invention to any theory or mechanism, it is believed that the present invention is advantageous because it features a small and compact enclosure that allows fewer lights (or smaller lights) to be used while allowing visual access to the infant.

The following the disclosures of the following U.S. patents are incorporated in their entirety by reference herein: U.S. Pat. No. 5,006,105; U.S. Pat. No. 4,809,677; U.S. Pat. No. 7,442,163; U.S. Pat. No. 5,446,934; U.S. Pat. No. 3,858,570; U.S. Pat. No. 7,008,371; U.S. Pat. No. 6,905,457; U.S. Pat. Application No. 2007/0088410; U.S. Pat. No. 5,792,214.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An enclosed bed device for providing phototherapy to infants, said enclosed bed device comprising:
   (a) a small bed base having a bottom surface and side walls that together form a base enclosure, wherein a base pad is disposed in the base enclosure, the base pad is a comfortable pad on which an infant is placed;
   (b) a lid pivotally attached to the bed base via a pivot means, the lid can pivot between multiple positions including an open position and a closed position respectively allowing and preventing access to the base enclosure of the bed base, the lid comprises a top surface and side walls that together form a lid enclosure;
   (c) one or more first fluorescent lights disposed in the lid enclosure and one or more second fluorescent lights disposed in the base pad, the first fluorescent lights and second fluorescent lights are operatively connected to a power source;

(d) a mesh cloth cover wrapped over the base pad, the mesh cloth cover is adapted to allow light from the second fluorescent lights in the base pad to pass from the base pad to the infant atop the base pad;

(e) a floor base and a stem extending upwardly from the floor base, the bed base is disposed atop the stem, the stem is adjustable in length via a manual or electronic mechanism, wherein three or more wheels are disposed on the floor base for allowing transport of the enclosed bed device, one or more drawers or cabinets are disposed in either the stem or floor base; and (f) a control panel operatively connected to the first fluorescent lights and second fluorescent lights for turning the lights on and off and for manipulating intensity of the lights;

wherein the base or lid either (i) is generally translucent, transparent, semi-translucent, semi-transparent, or tinted for viewing; or (ii) comprises a window for providing visual access.

2. The enclosed bed device of claim 1 further comprising one or more slots disposed in the base to allow cords to easily pass in and out of the base.

3. The enclosed bed device of claim 1, wherein the lid is pivotally attached to a first side edge of the bed base.

4. The enclosed bed device of claim 1 further comprising a handle disposed on the lid.

5. The enclosed bed device of claim 1, wherein the second fluorescent lights are fiber optic cords that run through the base pad.

6. The enclosed bed device of claim 1, wherein the first fluorescent lights and second fluorescent lights are operatively connected to an electrical outlet via a plug.

7. The enclosed bed device of claim 1, wherein the stem comprises an inner pole telescopically received in an outer pole.

8. The enclosed bed device of claim 1 further comprising a heating system for helping to warm the infant when in the bed device.

9. The enclosed bed device of claim 8 further comprising a temperature gauge or thermometer for measuring temperature in the base.

10. The enclosed bed device of claim 1 further comprising an IV pole holder disposed on the base.

\* \* \* \* \*